United States Patent [19]
Braun

[11] Patent Number: 6,127,111
[45] Date of Patent: *Oct. 3, 2000

[54] LYOPHILIZED PLATELET COMPOSITION CONTAINING CHLOROQUINE, HYDROXYCHLOROQUINE, CAMOQUIN, QUINACRINE OR PROCAINE

[75] Inventor: Konrad Braun, Ebsdorfergrund, Germany

[73] Assignee: Dade Behring Marburg GmbH, Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/915,558

[22] Filed: Aug. 21, 1997

[30] Foreign Application Priority Data

Aug. 24, 1996 [DE] Germany .......................... 196 34 313

[51] Int. Cl.$^7$ .............................. A01N 1/02; A01N 63/00
[52] U.S. Cl. ............................................. 435/2; 424/93.72
[58] Field of Search .............................. 435/2; 424/93.72

[56] References Cited

U.S. PATENT DOCUMENTS

| | | | |
|---|---|---|---|
| 4,405,719 | 9/1983 | Crews et al. | |
| 5,213,814 | 5/1993 | Goodrich, Jr. et al. | 424/532 |
| 5,641,637 | 6/1997 | Hudak et al. | 435/7.24 |
| 5,651,966 | 7/1997 | Read et al. | 424/93.72 |
| 5,736,313 | 4/1998 | Spargo et al. | 435/2 |

FOREIGN PATENT DOCUMENTS

| | | |
|---|---|---|
| 0 433 927 A2 | 6/1991 | European Pat. Off. . |
| 61-249924 | 11/1986 | Japan . |
| WO 93/23997 | 12/1993 | WIPO . |
| WO 96/13158 | 5/1996 | WIPO . |

OTHER PUBLICATIONS

Murakami et al., "Potentiating Effect of Adenosine on Other Inhibitors of Platelet Aggregation", Thrombosis et Diathesis Haemorrahagica 27(2) : 252–62 (1972).

Lehninger, "Biochemistry" Third Edition, Chapter 11, p. 217 (1971).

Glusa et al., "Platelet functions in recombinant hirudin–anticoagulated blood", Haemostasis 20 (2) : 112–8 (1990).

Bode et al., "The use of thrombin inhibitors and aprotinin in the preservation of platelets stored for transfusion" J. Lab. Clinical Med. 113 (6) : 753–8 (1989).

Prowse et al., "Prevention of the platelet alpha–granule release reaction by membrane–active drugs", Thrombosis Research 25 (3) : 219–27 (1982).

Abernathy et al.;"Pooled Donor Control For Platelet Aggregometry" Thrombos. Haemostas. (Stuttg.), 39, p. 246 (1978).

Greinacher et al.; "A Rapid and Sensitive Test for Diagnosing Heparin–Associated Thrombocytopenia" Thrombosis and Haemostasis 66(6), (Sututtgart) pp. 734–736 (1991).

Greinacher et al.; "Laboratory Diagnosis of Heparin–associated Thrombocytopenia and Comparison of Platelet Aggregation Test, Heparin–induced Platelet Activation Test, and Platelet Factor 4/heparin Enzyme–linked immunosorbent Assay" Transfusion; vol. 34, No. 5, pp. 381–385, (1994).

Jackson et al.; "Management of Thrombocytopenia" Haemostasis and Thrombosis, [Colman et al.] J. B. Lipincott Co., 2nd Ed. Chapter 28, pp. 530–536 (1987).

White; Drug Treatment and Prevention of Malaria; "European Journal of Clinical Pharmacology" 34(1), pp. 1–14 (1988).

Bode et al., "The Use of Inhibitors of Platelet Activation or Protease Activity in Platelet Concentrates Stored for Transfusion", *Blood Cells*, 18, pp. 361–380 (1992).

*Primary Examiner*—Sandra E. Saucier
*Attorney, Agent, or Firm*—Finnegan, Henderson, Farabow, Garrett & Dunner, L.L.P.

[57] ABSTRACT

The present invention relates to preparations of functionally active platelets and to a process for stabilizing these functionally active platelets by means of freeze-drying. In particular, a lyophilized or reconstituted platelet composition containing an anticoagulant, an cake forming agent ad an inhibitor of platelet function selected from the group consisting of chloroquine, hydroxychloroquine, camoquin, quinacrine and procaine is disclosed.

21 Claims, No Drawings

LYOPHILIZED PLATELET COMPOSITION CONTAINING CHLOROQUINE, HYDROXYCHLOROQUINE, CAMOQUIN, QUINACRINE OR PROCAINE

The present invention relates to preparations or functionally active platelets and to a process for stabilizing these functionally active platelets by means of freeze-drying.

BACKGROUND OF THE INVENTION

Functionally active platelets are of value both with regard to diagnosis and with regard to therapy. An example of an aspect of using a preparation of functionally active platelets is that of employing the preparation as control material for platelet function diagnosis. Aggregometry plays the most important part in this diagnosis. The diagnosis involves measuring the reaction of fresh platelets, which are as a rule present as platelet-rich plasma, to various inducers, in particular ADP, adrenaline, arachidonic acid, collagen and thrombin. The reaction is normally measured using the known turbidimetric methods. The inducers (apart from adrenaline) first of all bring about a change in the shape of the cells, with this change being recognizable by a transient increase in the extinction. Aggregation subsequently takes place. Biphasic aggregation curves often result. The second phase is closely linked to the release reaction and to prostaglandin synthesis. Arachidonic acid and collagen induce only monophasic aggregation curves as an expression of irreversible aggregation.

The investigation of platelet function has nowadays been extensively automated for reasons of rationalization and precision. It is absolutely necessary to have a quality control strategy for assessing the results. Hitherto, the only option for controlling this diagnosis has been that of using a pool of samples from "normal" donors (Abernathy et al. (1978) Throm.Haemostas. 39, p. 246).

For a laboratory, this is a control material which can only be prepared with a great deal of effort and expense. While a stable and functionally active platelet preparation having defined and constant properties is desirable for controlling platelet function, such a preparation has not hitherto been available.

Another aspect of the use of stable, functionally active platelets is their use in diagnostic test methods in which platelets are one of the reagents to be employed in the method. One example of such methods are tests for diagnosing heparin-associated thrombocytopenia (HAT). This is a rare (approx. 5%) but serious complication of antithrombotic therapy with heparins. Nonimmunological forms (HAT I) are distinguished from immunologically determined forms (HAT II). In contrast to other medicinally induced thrombocytopenias, which as a rule provoke bleeding complications, HAT results in thromboembolic complications which can extend to the occlusion of large blood vessels. Various diagnostic approaches are used for the early diagnosis of a type II HAT. Apart from counting platelets, which is an initial exploratory test, and the serotonin release test as the reference method, a test for heparin-induced platelet aggregation (HIPA) is particularly suitable, which test approaches the reference method in sensitivity and specificity (Greinacher et al. (1991) Thromb.Haemostas.6616),734(1991) Greinacher et al. (1994) Transfusion 34, p. 381). This test investigates whether the patient plasma can cause thrombocytes from healthy donors to aggregate under suitable conditions (low heparin concentration). The preparation of the thrombocytes, which necessitates the pooling of platelet-rich plasma from several healthy donors, is very expensive and time-consuming for a laboratory and has previously stood in the way of introducing the test into laboratory routine. A preparation of stable thrombocytes which are still functionally active to the extent that they can be aggregated under suitable conditions would substantially simplify and accelerate implementation of this test.

Therapeutically, platelet concentrates can be used for treating disturbances of platelet function which are of varying origin. Platelet concentrations of<70,000 per microliter are referred to as thrombocytopenias. Thrombocytopenias are due either to insufficient production of platelets, to an accelerated degradation of these cells or to abnormal distribution (Colman et al. (1987) Haemostasis and Thrombosis (J. B. Lipincott Co.) 2nd Ed., Chapter 28). In principle, inadequate platelet function can be genetically determined (e.g.: Glanzmann's thrombasthenia or Bernard-Soulier syndrome) or be acquired (e.g. failure of the bone marrow in association with malignant diseases, chemotherapy or disseminated intravasal coagulation). A number of drugs, pharmaceuticals and ionizing radiations can lead to acquired thrombocytopenias.

Patients who suffer from a thrombocytopenia have a bleeding tendency which is similar to hemophilia. As a rule, the bleeding is from capillary blood vessels; a typical example is relatively minor bleeding into the mucous membranes (petechiae). Normally, minor damage to the capillary vessel wall is sealed by agglutinating platelets.

Nowadays, patients having low platelet numbers are treated by infusion of platelet concentrates. These concentrates typically contain $6 \times 10^{10}$ platelets in approx. 50 ml of plasma. They are prepared by centrifuging anticoagulated blood in a stepwise manner and taking up the platelet sediment once again into plasma. Alternatively, platelet concentrates can be prepared using an apheresis apparatus, which separates the platelets directly from blood. Under suitable conditions (room temperature), platelet concentrates will keep for up to 7 days. During storage, the bags which contain the concentrate have to be maintained constantly in motion.

Although it would be desirable if the platelet concentrates kept for a longer period, it has not previously been possible to achieve this.

A first possible strategy for increasing the durability of platelet concentrates for diagnostic or therapeutic purposes consists in switching off particular mechanisms for activating the platelets. This is intended to ensure that the platelets are not prematurely activated, by the process of their being enriched and stored, to secrete ingredients and to aggregate. Various strategies of this nature are described in the literature; these strategies extend from defined washing procedures through to the addition of specific inhibitors:

Calcium, which is an activator of platelet aggregation, can be complexed by a chelating agent, for example EDTA.

The activator ADP can be broken down completely to AMP by adding the enzyme apyrase.

Plasma factors which might contribute to platelet activation can be removed by washing the platelets.

Thrombin can be inhibited by adding hirudin or heparin/antithrombin III.

The addition of prostacyclin ($PGI_2$) prevents platelet aggregation by means of stimulating the cellular adenylate cyclase.

Aspirin or indomethacin inhibit the cyclooxygenase of the platelets and thereby irreversibly switch off the route for synthesizing thromboxane.

However, it has been found in practice that adding the inhibitors irreversibly damages the platelets or inhibits them powerfully in their function. There is a need for a method for stabilizing these cells in a gentle manner without significantly impairing their function.

Any stabilizing method must ensure that the platelets retain a certain degree of functional activity throughout the entire process; this includes ensuring, for example, that the platelets do not alter their shape, do not excrete activators and do not aggregate during the preparation and stabilization of the concentrate. In a stable platelet preparation, the platelets should be present as individual cells having a predominantly discoid shape. The functional activity presupposes the retention of certain cell organelles (e.g. a-granula) and, at the molecular level, the retention of certain receptors on the cell-surface, for example glycoprotein Ib/IX, which serves as the receptor for the von Willebrand factor, or glycoprotein IIb/IIIa, which serves as the receptor for fibrinogen. It is furthermore necessary for certain metabolic pathways which release messenger substances in response to the binding of ligands to the receptors and which set in motion physiological processes, for example secretion from a-granula, to remain intact.

Platelets which have been stabilized by freeze-drying have already been described, although these platelets only react in an appropriate manner to activation by von Willebrand factor.

Consequently, the present invention was based on the object of making available a platelet preparation which, meets the above-described requirements.

BRIEF SUMMARY OF THE INVENTION

Surprisingly, it was found that it was possible to obtain functionally active platelets, which exist as individual cells, after adding particular-inhibitors or stabilizers and then freeze-drying.

DETAILED DESCRIPTION OF THE INVENTION

Within the sense of the present invention, functionally active means, that the stabilized and reconstituted platelets at least react to the addition of any of the following substances by secreting platelet-specific substances, by altering their geometric shape, by agglutinating or by aggregating.

ADp, calcium, collagen, arachidonic acid, thrombin, antibodies against platelet constituents, and platelet activators from the coagulation cascade. Platelets are also preferred which react specifically to individual substances from this list, or to selected combinations thereof. Platelets are particularly preferred which react to the addition of heparin.

Consequently, the invention relates to a process for obtaining functionally active platelets in which blood is first of all withdrawn and mixed with an anticoagulant. Suitable anticoagulants in this context are the generally customary anticoagulants such as citrate or EDTA, which are employed in the concentrations which are customarily used. In a preferred manner, inhibitors can be included in the withdrawal medium. For example, it is advantageous to include thrombin inhibitors at a concentration which ensures that all the thrombin which can be formed in the blood is securely inhibited. It is particularly advantageous to use hirudin at a final concentration of from 1 unit/ml to 10 units/ml. It is also possible to include platelet function inhibitors. Surprisingly, the substance hydroxychloroquine sulfate is suitable for use as an inhibitor of platelet function in addition to the above-discussed specific inhibitors of platelet function. Chloroquine and hydroxychloroquine are known as anti-malarial agents. They are cationic amphiphilic drugs which are fully able to traverse the cell membrane. Millimolar concentrations of hydroxychloroquine sulfate, preferably of from 0.1 to 5 g/l, particularly preferably of 5 g/l, are suitable for stabilizing the platelets.

The platelets are separated from the anticoagulated blood by means of sequential centrifugation using methods which are known as such to the skilled person. In a first step, a centrifugation is, for example, carried out at 3000×g for 45 minutes; platelets are obtained by separating off the buffy coat, and are taken up in a buffered solution of anticoagulant. This material is centrifuged at 200×g for 20 minutes in order to separate off other blood cells; platelets form the supernatant.

These platelets are now washed several times with an excess of washing buffer. The washing buffer contains anticoagulants, buffering substances and stabilizers. Examples of suitable anticoagulants are EDTA or citrate. The buffering can also be effected with citrate or other buffer systems (HEPES or phosphate). The washing buffer can preferably have the following composition: 32.2 g of sodium citrate/l, 5 g of hydroxychloroquine sulfate/l, pH 7.4.

A cake-forming agent for the lyophilization is then added to the platelet suspension as well. A polysaccharide, for example mannitol, or a protein, for example polygeline or serum albumin, is advantageous. Preferably, serum, albumin is employed at a final concentration of from 0.1 to 100 g/l, very preferably from 10 to 70 g/l, particularly preferably 50 g/l.

Finally, the platelets are adjusted to a concentration of between $10^4/\mu l$ and $10^8/\mu l$, preferably to $10^7/\mu l$.

The platelets are advantageously incubated for from 5 to 60, preferably for from 10 to 40, very preferably for about 30 minutes at room temperature (from 10 to 40, preferably from 20 to 25° C.) and then freeze-dried such that a residual moisture content is obtained which is between 0% and 10%, and is preferably about 3%.

The combined addition of an inhibitor and a cake-forming agent is particularly advantageous. This evidently stabilizes the platelets insofar as they can be activated by physiological activators after having been frozen down and freeze-dried.

For reconstitution, the freeze-dried platelet concentrate is advantageously reconstituted in activation buffer.

This contains, for example:

Glucose at a concentration of between 0 g/l and 100 g/l, preferably of from 1 g/l to 10 g/l, particularly preferably of about 2.4 g/l, a magnesium salt, preferably magnesium chloride, at a concentration of between 0 g/l and 100 g/l, preferably of from 1 g/l to 5 g/l, particularly preferably of about 1.2 g/l, a potassium salt, preferably potassium chloride, at a concentration of between 0 g/l and 100 g/l, preferably of from 1 g/l to 5 g/l, particularly preferably of about 1.6 g/l, a sodium salt, preferably sodium chloride, at a concentration of between 0 g/l and 100 g/l, preferably of from 0.5 g/l to 5 g/l, particularly preferably of about 0.6 g/l.

In order to remove inhibitors of platelet function, the platelets can also be washed in the abovementioned activation buffer, for example by being suspended and centrifuged down at about 2400×g.

After these steps, the platelet concentrate can be employed as a standard material for platelet function tests or as a reagent in diagnostic tests.

The freeze-dried platelets will keep at +4° C. for at least 6 months. The storage does not impair the aggregometrically measured reactivity of the platelets to activators, for example collagen or thrombin. Consequently, stability is improved by at least a factor of 30 as compared with the durability of liquid platelet concentrates (7 days).

Freeze-dried platelets can also be employed as a medicament for treating platelet deficiencies or platelet malfunctions.

In order to prepare a therapeutically utilizable composition, the platelets have to be formulated in a suitable form. Pharmaceutically utilizable carrier systems which are known per se to the skilled person are used for this purpose. Preferably, the platelets are administered intravenously as a sterile suspension. The freeze-dried material comprises activatable platelets, as the therapeutically active material, and also hydroxychloroquine sulfate and serum albumin as stabilizers. A medicament which can be employed pharmaceutically directly is already obtained by resuspending in sterile water for injection. Extensive experience exists in the use of both hydroxychloroquine sulfate and serum albumin in man. Hydroxychloroquine sulfate is a drug for malaria therapy which has been known for a long time (Webster (1990) in: The Pharmacological Basis of Therapeutics; Eds. L. S. Goodman and A. Gilman, 8th Edtn.). While its route of use is oral as a rule, intravenous use is also possible (White (1988) Eur.J.Clin.Pharm. 34(1), p.1–14). At the concentration of hydroxychloroquine sulfate of about 5 g/l which is preferably used, and at a platelet concentration of $10^7/1 \mu l$, the infusion of the platelet number which is normally contained in one liter of blood would be associated with the intake of 250 mg of hydroxy-chloroquine sulfate. During malaria therapy, up to 500 mg of the substance are used per day. The intravenous administration of 0.8 mg per kg and hour is toxicologically harmless (White 1988). It can therefore be assumed that the addition of hydroxychloroquine sulfate to the platelets is toxicologically harmless.

Human serum albumin is a well known and toxicologically harmless stabilizer which is contained in many approved pharmaceuticals.

In addition to infusing the freeze-dried platelets directly after dissolution in sterile water for injection, other formulations of the platelets for use in patients are also possible. Thus, the hydroxychloroquine sulfate, for example, can be removed by washing, where appropriate several times, the platelets which have initially been resuspended in water. For this, the platelets have to be centrifuged down at about 2400×g and then taken up in a pharmaceutically suitable medium. In principle, pharmaceutically suitable media of this nature are all the solutions which are known per se to the skilled person for this purpose, such as sterile salt solutions (for example isotonic NaCl or other salt solutions), sterile buffer solutions (citrate, Tris or HEPES) and sterile solutions of stabilizers (proteins such as human serum albumin or other proteins, or sugars such as mannitol or other sugars).

The following examples are intended to clarify the invention.

EXAMPLES

EXAMPLE 1.1

Preparation of a Platelet Concentrate from Citrate Blood

Blood is withdrawn from healthy donors by means of venous puncture and mixed directly with anticoagulant. This is done by filling a flask, which already contains 50 ml of concentrated citrate buffer (39.6 g of sodium citrate/l+0.26 g of citric acid/l, pH 7), with 500 ml of blood while avoiding foam formation. The flask is shaken carefully in order to mix the contents. The blood is transferred to a stainless steel bucket and centrifuged at approx. 3000×g for 45 minutes at 12° C.–18° C. The overlying plasma is discarded. The cell layer immediately below, i.e. the buffy coat, is taken up in washing buffer (32.2 g of sodium citrate/l, 5 g of hydroxychloroquine sulfate/l, pH 7.4) and centrifuged twice at 200×g for 20 minutes in order to separate off leucocytes. The supernatant forms a thrombocyte suspension. The cells are subsequently washed a further two times with washing buffer. For this, the suspension is first of all centrifuged down at 2400×g for 20 minutes and then in each case resuspended in washing buffer.

EXAMPLE 1.2

Freeze-drying a Platelet Concentrate

A platelet suspension is prepared as described in Example 1.

The platelet density is determined using an automated counter (Möab, Hilden, Germany). The suspension is then adjusted with washing buffer to $5 \times 10^7/\mu l$.

50 mg of bovine serum albumin are added per ml of the suspension. The suspension is then used to fill appropriate containers and freeze-dried under mild conditions. The highest temperature which is set is 40° C. and the drying lasts for a total of 25 hours. The process is carried out in such a way that a residual moisture content of approx. 1–2% is obtained.

EXAMPLE 2

Aggregation of Platelets with Collagen after Freeze-drying

Platelets were prepared and freeze-dried as described in Example 1. The lyophilisate is reconstituted in the original volume of distilled water.

The platelets are centrifuged down by centrifuging at 2500×g for 10 minutes and taken up in the same volume of isotonic sodium chloride solution; they are then washed twice in this solution. The platelets are subsequently taken up in activation buffer (2.4 g of glucose/l, 0.6 g of NaCl/l, 1.2 g of $MgCl_2$/l, 1.6 g of KCl/l) and adjusted to a concentration of $4.6 \times 10^5/\mu l$ using this buffer. The platelets are counted using an automated counter (from Mölab, Hilden, Germany).

Platelet-rich citrate plasma (pooled from healthy donors) which is adjusted to $4.8 \times 10^5/1 \mu l$ with platelet-poor plasma is used as the positive control. Platelets which have been fixed in 4% formalin and then lyophilized are used as the negative control. These platelets are reconstituted in isotonic NaCl solution and adjusted to $4.9 \times 10^5/\mu l$.

1000 $\mu l$ of platelets are mixed either with 100 $\mu l$ of human placenta collagen (1 mg/ml, Behring Diagnostics, Marburg, Germany) or with 100 $\mu l$ of isotonic NaCl, as control, and incubated at 37° C. for 15 minutes. The mixtures are then centrifuged at 40×g for 10 minutes in order to separate off aggregates.

The platelet density in the supernatant is determined in each case and is a measure of the proportion of platelets which cannot be aggregated.

TABLE 1

| | Platelet density in the supernatant | |
|---|---|---|
| Activator | NaCl (negative control) | Collagen |
| Platelet-rich plasma (positive control) | 85 | 9 |
| Fixed platelets (negative control) | 77 | 74 |
| Stabilized and lyophilized platelets | 70 | 3 |

It is found that, under the conditions chosen, the platelets from platelet-rich plasma and the lyophilized platelets are present almost entirely in the form of separable aggregates, whereas the formalin-fixed platelets cannot be aggregated.

EXAMPLE 3

Aggregation of Platelets with Thrombin After Freeze-drying

Platelets were prepared and freeze-dried as described in Example 1. The lyophilisate is reconstituted in the original volume of distilled water.

The platelets are centrifuged down by being centrifuged at 2500×g for 10 minutes and taken up in the same volume of isotonic sodium chloride solution; they are then washed twice in this solution. The platelets are subsequently taken up in activation buffer (2.4 g of glucose/l, 0.6 g of NaCl/l, 1.2 g of MgCl$_2$/l, 1.6 g of KCl/l) and adjusted to a concentration of $4.6 \times 10^5/\mu l$ using this buffer. The platelets are counted with an automated counter (from Mölab, Hilden, Germany).

Platelets which have been fixed in 4% formalin and then lyophilized are used as the negative control. These platelets are reconstituted in isotonic NaCl solution and adjusted to $4.7 \times 10^5/\mu l$.

1000 $\mu l$ of platelets are preincubated at 37° C. for 5 minutes. Purified bovine thrombin (100 $\mu l$, 3 IU/ml; Behring Diagnostics) or 100 $\mu l$ of isotonic NaCl are then added. Incubations are carried out at 37° C. for 15 minutes. The mixtures are then centrifuged at 40×g for 10 minutes in order to separate off aggregates.

The platelet density in the supernatant was determined in each case and is a measure of the proportion of platelets which cannot be aggregated.

TABLE 2

| | Platelet density in the supernatant | |
|---|---|---|
| Activator | NaCl (negative control) | Thrombin |
| Fixed platelets (negative control) | 64 | 64 |
| Stabilized and lyophilized platelets | 65 | 19 |

It is found that, under the conditions chosen, about two thirds of the lyophilized platelets are present in the form of separable aggregates, whereas the formalin-fixed platelets cannot be aggregated.

What is claimed is:

1. A lyophilized platelet-containing composition comprising an inhibitor of platelet function and containing about 10% by weight or less moisture, prepared by lyophilization of an aqueous suspension of platelets in a medium comprising a) an anticoagulant, b) a cake-forming agent, and c) an inhibitor of platelet function selected from the group consisting of chloroquine, hydroxychloroquine, camoquin, quinacrine and procaine, and wherein said anticoagulant and said inhibitor of platelet function are different substances.

2. The composition of claim 1, wherein said anticoagulant is selected from the group consisting of citrate, EDTA, and hirudin.

3. The composition of claim 2 wherein said anticoagulate is hirudin.

4. The composition of claim 3 wherein said hirudin is in a concentration of between 0.1 and 10 U/ml.

5. The composition of claim 1, wherein said platelet inhibitor is hydroxychloroquine.

6. The composition of claim 5, wherein said hydroxychloroquine is in a concentration of between 0.1 and 100 g/.

7. The composition of claim 1, wherein said cake forming agent is chosen from a protein of polysaccharide.

8. The composition of claim 1, wherein said cake-forming agent is at least one of serum albumin, mannitol, or polygeline.

9. The composition of claim 8, wherein said serum albumin is in a concentration of between 0.1 and 100 g/l.

10. The composition of claim 8, wherein said serum albumin is in a concentration of between 10 and 70 g/l.

11. The composition of claim 1 further comprising the step of reconstituting the freeze-dried platelets by suspending said platelets in an activation buffer followed by centrifugation.

12. The composition of claim 11, wherein the activation buffer comprises at least one of glucose at a concentration of 1 mg/l to 100 g/l, a magnesium salt at a concentration of 1 mg/ to 100 g/l, a potassium salt at a concentration of 1 mg/l to 100 g/l, and a sodium salt at a concentration of 1 mg/l to 100 g/l.

13. The composition of claim 12, wherein the activation buffer comprises glucose and said glucose is present in a concentration of 0.1 to 5 g/l.

14. The composition of claim 12, wherein the activation buffer comprises magnesium chloride in a concentration of from 0.1 to 5 g/l.

15. The composition of claim 12, wherein the activation buffer comprises potassium chloride in a concentration of from 0.1 to 5 g/l.

16. The composition of claim 12, wherein the activation buffer comprises sodium chloride in a concentration of from 0.1 to 5 g/l.

17. A reagent comprising platelets as claimed in claim 11.

18. The reagent as claimed in claim 17 which is used as a standard or control material for platelet function tests.

19. The reagent as claimed in claim 17 which is employed for detecting heparin-induced thrombocytopenia.

20. A pharmaceutical composition for treating inadequate platelet function in a patient comprising dissolving the freeze-dried platelets as claimed in claim 1 in sterile water for administration to said patient.

21. A pharmaceutical composition comprising the freeze-dried platelets as claimed in claim 1 and a pharmaceutically acceptable carrier.

* * * * *